(12) United States Patent
Brady

(10) Patent No.: US 8,822,927 B2
(45) Date of Patent: Sep. 2, 2014

(54) DROPLET COUNTING AND MEASURING DEVICE

(75) Inventor: Michael Brady, Billericay Essex (GB)

(73) Assignee: Billericay Farm Services Limited (GB)

( * ) Notice: Subject to any disclaimer, the term of this patent is extended or adjusted under 35 U.S.C. 154(b) by 121 days.

(21) Appl. No.: 13/393,641

(22) PCT Filed: Sep. 3, 2010

(86) PCT No.: PCT/GB2010/051468
§ 371 (c)(1),
(2), (4) Date: Mar. 1, 2012

(87) PCT Pub. No.: WO2011/027167
PCT Pub. Date: Mar. 10, 2011

(65) Prior Publication Data
US 2012/0154787 A1    Jun. 21, 2012

(30) Foreign Application Priority Data
Sep. 3, 2009  (GB) .................................. 0915346.1

(51) Int. Cl.
*G01N 15/14*  (2006.01)

(52) U.S. Cl.
CPC .................................. *G01N 15/1459* (2013.01)
USPC ....................................................... 250/341.1

(58) Field of Classification Search
CPC ....................... G01N 15/1434; G01N 15/1459
USPC ......................................... 356/335; 250/341.1
See application file for complete search history.

(56) References Cited

U.S. PATENT DOCUMENTS

| 3,823,320 | A | * | 7/1974 | Ledoux ...................... 250/222.1 |
| 4,260,258 | A | * | 4/1981 | Rose et al. ..................... 356/335 |
| 2005/0000277 | A1 | | 1/2005 | Giles |
| 2007/0229825 | A1 | | 10/2007 | Bates |
| 2008/0049231 | A1 | | 2/2008 | Bachalo et al. |
| 2009/0312988 | A1 | | 12/2009 | Bachalo et al. |

* cited by examiner

*Primary Examiner* — Constantine Hannaher
(74) *Attorney, Agent, or Firm* — Renner Kenner Greive Bobak Taylor & Weber

(57) ABSTRACT

A device to measure the characteristics of droplets within a stream of liquid droplets used in spraying includes a light source supplying light across the stream of droplets; a detector to detect change in the light level caused by a passing droplet, the detector generating a signal according to the change in light; and a processor to analyze the characteristics of the droplets in the stream based on the signal produced by the detection means. The light passes through a slit in a panel disposed between the droplet stream and the detector, so that the change in level of light detected by the detector is proportional to the diameter of the droplet.

17 Claims, 4 Drawing Sheets

DROPLET COUNTING AND MEASURING DEVICE

Figure 1:
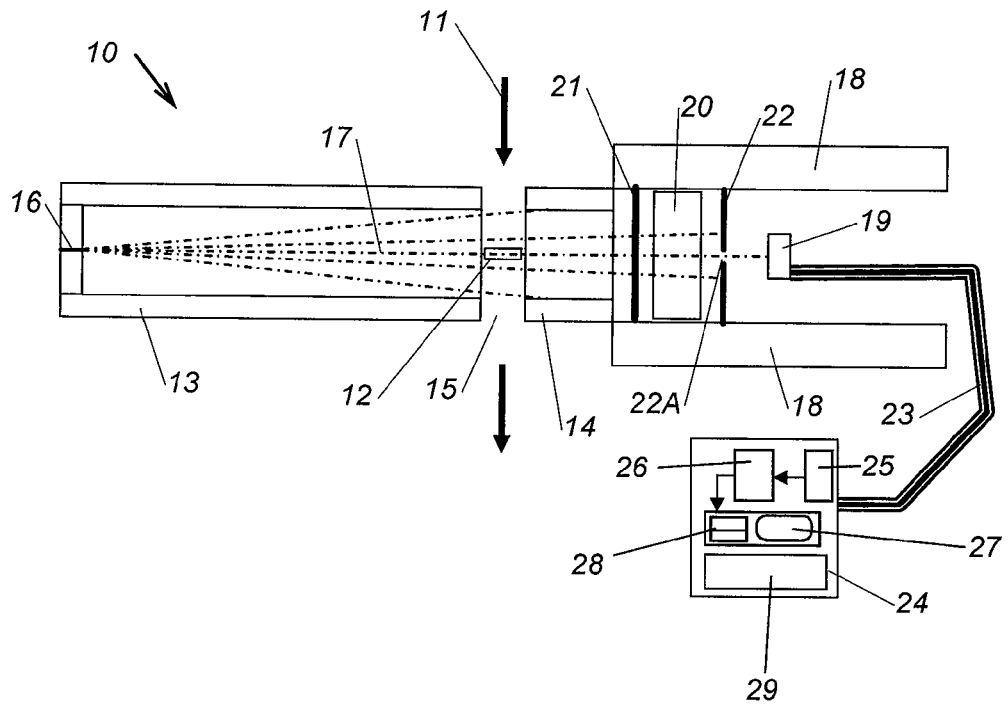

This invention relates to a device for measuring and counting droplets of liquid, and in particular, though not exclusively, to a device for measuring and counting droplets of liquid used for agricultural spraying.

In agriculture, regular crop spraying with pesticides and herbicides is essential to reduce the occurrence of insect pests, weeds and disease thereby to maintain high yields and good quality produce. The spraying can be done at any scale from manually with small hand pumped or battery driven hand held sprayers to a larger scale by self propelled spraying machines with powered pumps and multiple spray nozzles mounted on booms. The sprays used are usually water based with the addition of organic pesticides or herbicides.

The size of the spray droplets is a major factor in the effectiveness of the spray. For a given spray volume, large droplets will leave gaps between each droplet as they hit the target and very small droplets will be carried away by air currents. For crop spraying most of the spray volume will be made up of droplets with a diameter in the range of 100 to 500 µm.

There are a number of conflicting requirements for droplet size, and so a range of droplet sizes is often desirable. Small droplets provide the greatest area of coverage, and are usually the most effective, as they reduce cost because a minimum amount of pesticide is used. However, larger droplets have the benefit of minimal drift due to air currents, and therefore hit the target area with minimal contamination of nearby crops and surfaces resulting in minimal environmental impact. Large droplets will also progress further through thick crop foliage, and even to the ground as desired in some instances.

In practice, spraying in windless conditions is rare. Even if there is no wind, air currents are caused by the movement of the spraying equipment, particularly when using self-propelled sprayers, which may travel at 15 kph or more. Droplets of about 200 µm in diameter are favourable as their drift due to air currents is acceptable and the coverage per volume is good. Different types of spray nozzle produce different spray volumes and should produce most of their spray volume within a specific droplet size range. A spectrum of droplet sizes is important and should determine the choice of nozzle and operating procedure to suit the relevant application and environmental conditions. For example, rotating disc sprayers can produce droplets of uniform size and this would be ideal if the target were a flat plate. However, where the target is foliage a range of droplet sizes has been found to give a more complete coverage.

The measurement of the sprayed droplet diameter spectrum is essential for: the quality control of nozzle performance; the comparison of nozzle designs; improving the nozzle design; and assessing the affects of various spray formulations. A major difficulty is measuring individual droplets when a typical nozzle will produce 5 million droplets per second. At 0.5 m below the nozzle where the droplets are generally measured they are travelling at between 1.5 and 10 m/s and passing at up to 3000 droplets per square centimeter per second.

There are three commonly used methods to determine the droplet sizes, each of which has considerable disadvantages. The simplest and industry standard way of measuring the diameter of droplets is to collect them in oil in an open Petri dish. Dishes are positioned where the target would be and the spray is passed over them. The droplets are held intact on the oil in the dish for some time, and the size of each droplet is measured using a travelling microscope, or latterly an electronic scanning system, and recorded. About 2000 droplets must be measured to obtain statistically significant information necessary to define the nozzle performance, which is extremely time-consuming. Related methods use a dye in the spray, or water sensitive paper to estimate the spray coverage.

For convenience, speed, and real time measurement, spray droplet sizes can also be measured using laser diffraction. A laser beam is passed through the spray and the amount of laser light scattered is measured. By comparing the amount of scattered light with the un-scattered light, the proportion of droplets in each size band can be estimated, though not the number of droplets. Whilst these devices can be used to measure droplet sizes over a vast range and give an instant answer in any form, they suffer from some significant disadvantages. In particular, the instruments required are of high cost and are designed for use in laboratory conditions, and so could not be suitable for outdoor use. Further, the value of refractive index of spray material and its propellant must be known for the interpretation of results; this will depend on the spray formulation which will vary. Finally, if the spray volume is too small insufficient light is refracted for reliable results. If the volume is too great, multiple refraction can causes errors.

Finally, optical imaging uses scanning of a very fast photograph of the spray droplets to measure their diameter and other properties. A processor enables statistical data to be generated instantly and in multiple formats. The capability is similar to that of the laser diffraction method and much more than is required for analysis of agricultural sprays. This technique requires laboratory standard equipment, and as such is of relatively high cost.

The present invention overcomes the disadvantages of known methods of measuring droplet sizes by providing a device which can accurately measure the characteristics of droplets to determine the number, speed and droplet diameter of a spectrum of droplets in laboratory or field conditions, and which device is relatively inexpensive. An aim of this invention is to provide an accurate, simple low cost means of measuring the droplet size spectrum in real operating conditions.

According to the present invention there is provided a device to measure the characteristics of droplets within a stream of liquid droplets used in spraying comprising:

a light source supplying light across the stream of droplets to be analysed;

detection means to detect the change in the level of light caused by a droplet passing through the light produced by the light source, the detection means generating a signal according to the change in light incident thereon; and processing means to analyse the characteristics of the droplets in the stream based on the signal produced by the detection means;

wherein the light passes through a slit in a panel disposed between the droplet stream and the detection means, so that the change in level of light detected by the detection means is proportional to the diameter of the droplet.

The device of the present invention is particularly well suited for use in agricultural spraying and it is preferred that the device is particularly adapted for that purpose but its application is not limited to that field.

The stream of droplets pass through the device and preferably the device defines a sampling area through which droplets pass and through which light from the light source crosses the stream, so that only droplets within the sampling area are measured as they pass therethrough. A major feature of this invention is making the sampling area in which the droplets are measured small enough to include only one droplet at a time. By keeping this area as small as possible the device preferably measures only one droplet at a time thereby avoiding false readings. If the sampling area is small it is occupied for a high proportion of the time by no more than one droplet. Preferably the volume of the sampling area is approximately 0.002 cm$^3$ to 0.005 cm$^3$ and preferably 0.0025 cm$^3$, although this depends on the droplet size range being measured. The volume of the measuring space is controlled in part by the cross-sectional area of the stream of sprayed droplets, the height of the light beam (which is governed by the width of the slit in the panel), and the width of the light beam which may also be controlled by masking of the beam, or use of a parallel beam as explained in more detail below.

The light source could possibly produce light from anywhere within the infrared to ultraviolet range including visible light. However the light source will preferably emit infrared light so that the detection means will not be sensitive to ambient light. Infra red light of approximately 950 nm has been found to work well. A lack of sensitivity to ambient light is an advantage as the present invention can then be used in the field away from laboratory conditions. Indeed it could be mounted permanently on a sprayer. When each droplet passes through the beam of light from the light source, a shadow is cast on the detection means, which results in a reduced level of light being detected. To ensure that the shadow is clean, and that light is not reflected in the device and around the droplet to give a false reading, it is preferred that a point light source is used. Advantageously, the area of the point light source is about 0.1 mm$^2$.

The slit needs to be narrower than the width of the droplets that are to be measured so that the resulting shadow of the droplet on the detection means is in direct proportion to the diameter of the droplet, and also so that usually only one droplet is detected at any one time. It has been found that the optimum width of slit for use in detecting droplets of a size commonly used in agriculture is 50 μm. Of course, the size of slit can be altered depending on the size of droplets to be measured. So that the beam of light reaching the detector means can most optimally be analysed, it is preferred that that device further includes a lens to focus the light beam after passing through the spray and preferably before passing through the slit.

Any device that can detect the level of light could be used for the detection means but it is preferred that these comprise one or more photo cell. This produces an electrical signal that varies according to change in light level caused by a droplet passing through the light beam.

Once produced, the signal will preferably be processed so that a reading can be generated from which the results can be easily analysed. The device preferably further includes an amplifier which amplifies the signal from the detection means, and preferably further comprises a current to voltage converter to convert electrical current produced by the detection means signal into a voltage reading, which can be more easily used in the analysis.

The processor analyses the signal coming from the detection means to produce a reading that can be used to study the characteristics of each droplet. Whilst each signal is in direct proportion to the diameter of each droplet, further information can be obtained which is useful for analysing the droplet stream. The processor also preferably includes a counter to count the number of droplets that pass. The processor preferably further includes a comparator to separate droplets into different size ranges to enable a detailed droplet diameter spectrum to be generated.

The change in signal caused by a droplet may be displayed on an oscilloscope, which is one way to enable the time to cross the slit to be measured and hence measure the speed of the droplet. Such an oscilloscope may be a storage oscilloscope so that individual droplets can be monitored. This is one way on which droplets which are exceptional because of their diameter or speed can be identified and if appropriate removed from the calculations.

Figure 2:
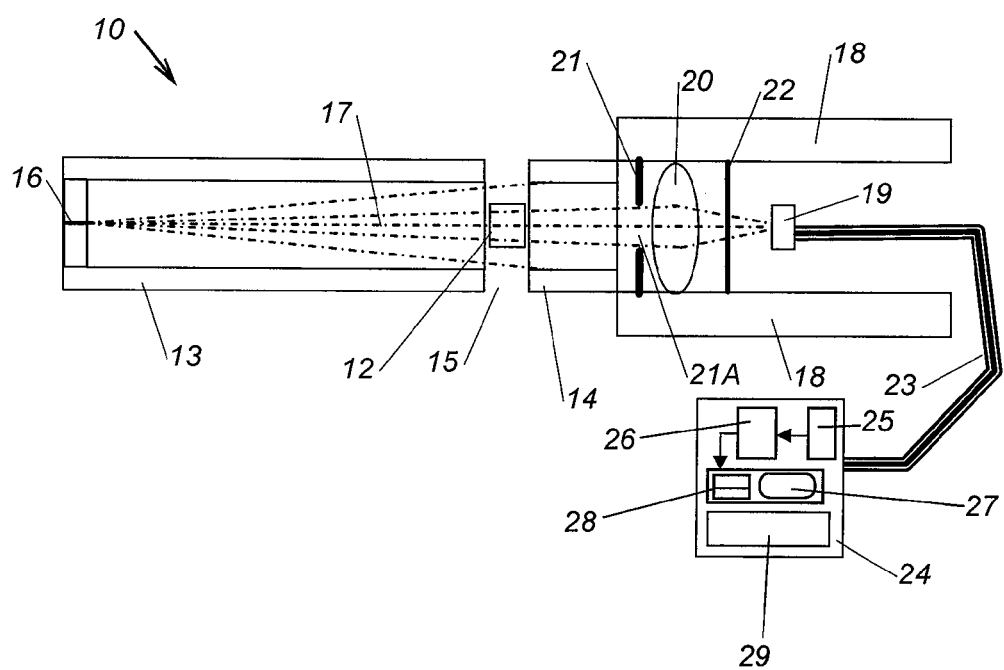

In an alternative embodiment, more than one measuring light beam may be passed through the droplet stream at different angles to improve accuracy. These angles are all perpendicular to the direction of droplet travel. To achieve this there may be further provided a second light source producing a second light beam perpendicular to the light from the first light source and convergent therewith as the second beam passes through the droplet stream; a second detection means to detect the change in the level of light in the second light beam; and a second panel with a slit disposed between the droplet stream and the second detection means. This second light source detector combination may have any of the features of the first light source discussed herein. It may be set up the same as the first or may be differently configured. Advantageously, only droplets equivalently detected by both or a majority (if more than 2 are used) detectors will be counted as this reduces errors from overlapping droplets.

The path of a light beam from the light source to the detector can be linear or non-linear. For example one or more mirror, prism or the like may be placed in a light path to change the direction of the beam of light. A first prism could be placed between the light source and the sampling area to turn the beam through 90° and a second prism could be placed after the sampling area to turn the light beam through a further 90° before the detector. This could allow the device to be more compact. The mirror or prism could be incorporated with other components such as the lens.

According to the present invention there is also provided a droplet measurement system comprising: one or more device as described above mounted on one or more sprayer; and a remote command unit that receives data from the or each device and which is adapted to analyse and/or display this to an operator. The devices may be wired to the command unit, but preferably they communicate wirelessly. More preferably the command unit controls several devices that are measuring droplets at several different locations simultaneously.

In order that it may be better understood, several embodiments of the present invention will now be described in detail, but by way of example only, with reference to the following drawings in which:

FIG. 1 shows a schematic side view of a first embodiment of droplet measuring device of the present invention;

FIG. 2 shows a schematic top view of the device shown in FIG. 1;

FIG. 3 shows an oscilloscope representation of the signal from the detection means as a droplet passes;

FIG. 4 shows a vertical section through a second embodiment of droplet measuring device;

FIG. 5 shows a plan view of a third embodiment of droplet measuring device;

FIG. 6 is a vertical section of the third embodiment of device along the line A-B in FIG. 5;

FIG. 7 is a representation of non-overlapping droplets in crossing light beams; and FIG. 8 is a representation of overlapping droplets in crossing light beams.

With reference to both FIGS. 1 and 2, there is shown a first embodiment of device, generally indicated 10 for measuring the characteristics, such as the quantity, size and velocity, of liquid droplets in a droplet spray stream. The present invention is particularly well suited to measuring droplets whose diameter's are in the range of 50 μm-1000 μm. FIG. 1 shows the path of the droplet stream generally indicated by arrows 11, and the droplet path direction in FIG. 2 would be normal to the page as viewed. The device comprises first and second tubular sections 13, 14, which are separated by a gap 15 through which the droplet stream to be measured passes. A measuring or sampling area 12 is defined in the gap 15 and only droplets passing through this are detected.

At one end of the first tubular section 13 is a point light source 16, which generates a beam of light, indicated by broken lines 17, which passes along the interior of the first tubular section 13 through the droplet stream 11 and then along the interior of the second tubular section 14. The light source 16 produces an infrared light beam, as this permits the device to be used in ambient light without interference, though light sources of other wavelengths could also be used.

The second tubular section 14 is adjacent a body section 18 which contains a photo detector 19 which produces a signal when hit by the beam of light. The signal produced by the photo detector 19 changes according to the level of light received thereon. Droplets passing through the beam of light will cause a change in the amount of light received by the photo detector 19, which will produce a varying signal. The signal produced by the photo detector varies in proportion to the characteristics of the droplets in the stream as they pass. There is also provided in the body section a cylindrical lens 20, a mask 21, and a plate 22. The cylindrical lens 20 acts to focus the light beam along one axis onto the photo detector 19 once it has passed through the droplet stream.

The mask 21 is positioned before the lens and comprises opposed plates that define a vertical slit 21A, and it may be adapted to block light that has not passed through the sampling area, so that only light that has passed through the sampling area proceeds to the lens 20. In effect it limits the beam width and defines one dimension of the sampling area 12. The plate 22 is disposed between the lens 20 and the photo detector 19, and has a narrow slit 22A that in this embodiment is 50 μm wide (although shown proportionally larger in the drawing for illustrative purposes). The narrow slit 22A extends horizontally and is dimensioned so that droplets passing through the gap 15 cause a change in light falling on the detector 19 that is directly in proportion to the diameter of the droplet. The width of the slit 22A defines another dimension of the sampling area 12.

An electrical cable 23 extends from the photo detector to a control box 24, which includes a DC amplifier 25 that amplifies the signal from the photo detector, and a current to voltage converter 26 to convert the signal into a voltage reading. The signal from the photo detector is fed into the current to voltage converter 26 and then the amplifier 25. The voltage reading is then analysed by a processor to determine one or more of the diameter, number and speed of the droplets. The control box 24 may also include a display from which information about the droplet stream can be obtained by an operator.

The light output from the source 16 may be set at such a level that a 500 mV signal is output from the amplifier when no occlusion in the gap occurs. The beam width where the droplets cross may be set (by the vertical slit 21A) to 7.0 mm. The device may be calibrated with a 1.00 mm rod which when inserted in the gap 15 where the droplet cross will reduce the light output signal by 500/7=71.4 mV. A droplet of 1000 μm (1.00 mm) diameter would therefore also reduce the signal by 71.4 mV, and one of 100 μm would reduce it by 7.14 mV.

The output signal may then be AC coupled to a further amplifier such that only the signal change due a passing droplet will be amplified. The AC amplification is adjusted so that a 1000 μm droplet would give a 5V signal.

Figure 3:
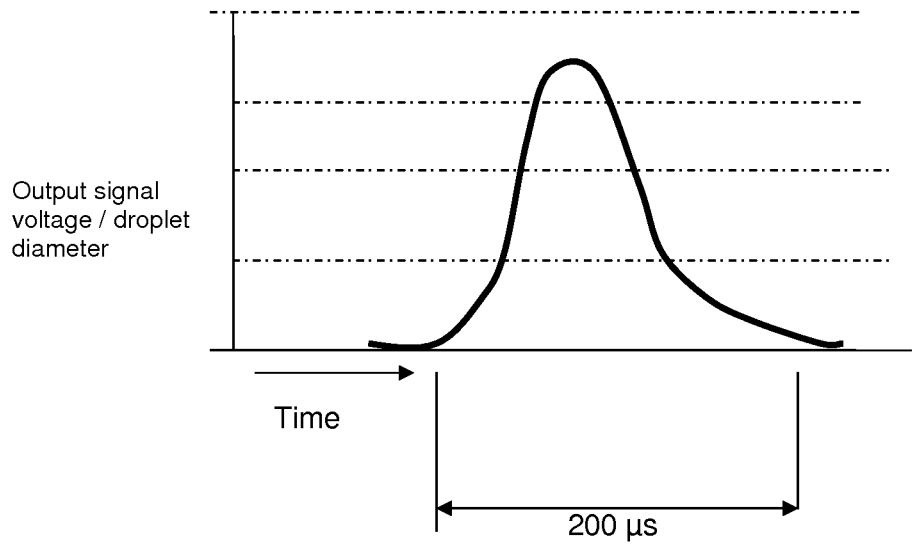

The droplets are usually travelling at about 2 ms$^{-1}$ so cast a shadow in the slit for a time dependent on their speed. The output signal as would appear on an oscilloscope 29 is shown in FIG. 3. The amplitude is proportional to droplet diameter and the baseline width is the time taken for the droplet to pass the slit. A droplet of diameter 350 μm passing the slit in 200 μs would have a speed of 2 ms$^{-1}$.

The output signal can be fed into a comparator 28 which would select droplet diameters exceeding a nominated value. The droplets giving a signal above the nominated value can be fed into a counter 27. Setting the comparator 28 to different values enables the number of droplets within a given range of diameters to be calculated and the droplet diameter spectrum derived.

Errors can occasionally occur due to two or more droplets casting a shadow over the slit at the same time. If the droplets pass the slit simultaneously side by side this will result in a wrongly recorded bigger droplet, but if one droplet is within the shadow of the other it will not be registered. A further error may occur when a droplet hits the edge of the sampling area and breaks up thereby incorrectly appearing as a number of smaller droplets. Similar errors can be present in the laser diffraction and photo imaging systems. Use of a second light source and detector where the beam passes through the stream perpendicular to the first will reduce or remove these errors.

A consequence of the sample area being only 50 μm deep is that as the droplets are generally bigger than this so the shadow size will be proportional to the droplet diameter. For droplets with a diameter less than 100 μm a correction to the size of the shadow might need to be made.

Figure 4:
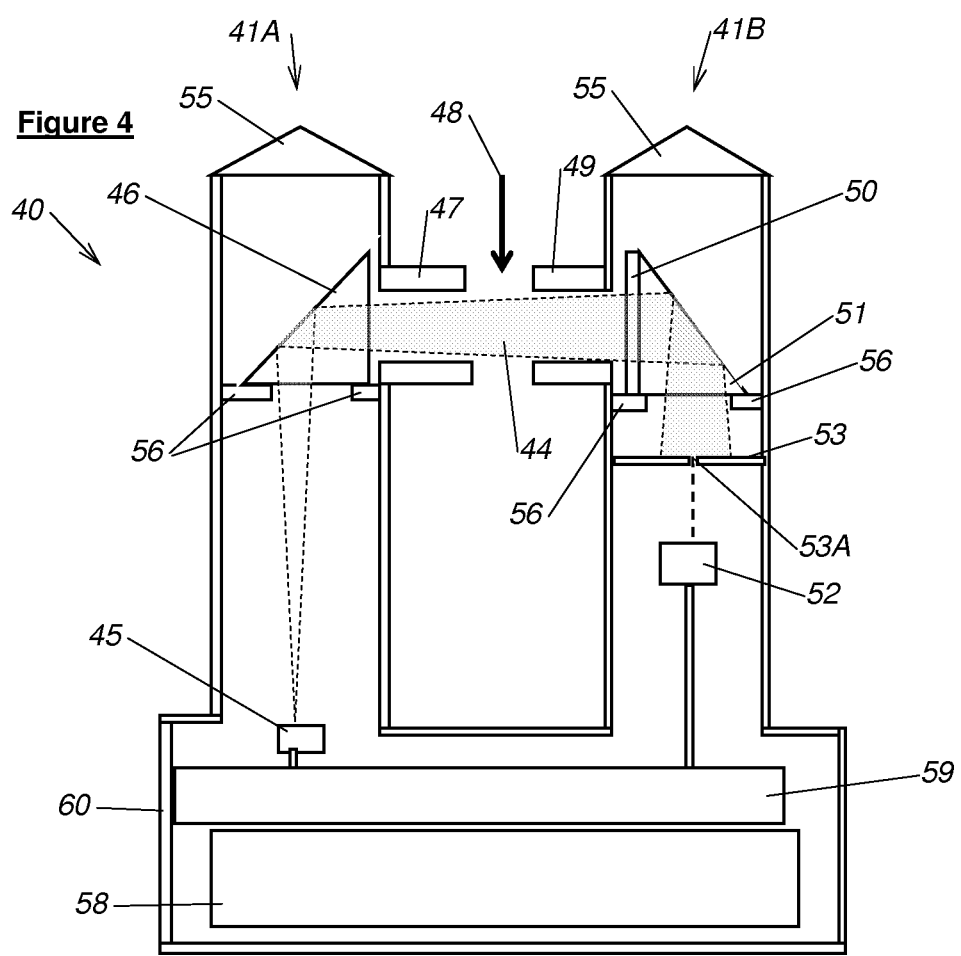

The simple arrangement of the first embodiment has disadvantages in that the shape is awkward for a portable monitor and there is some difficulty in sealing the photo optics from the spray medium. A second embodiment that gives a more compact unit with adequate protection of the photo optics is generally indicated 40 in FIG. 4. In this the slit has been moved so that it is behind a lens and prism so protected from the spray.

Within a transmitting turret 41A light is generated by an LED point source 45 with a small emitting area (less than 0.1 mm$^2$) and falls on the base of a first prism 46. The light is reflected and thereby rotated 90° by the prism 46, then travels along the transmitting beam tube 47 through the sampling area 44, where droplets travelling in the direction of arrow 48 pass. The light then passes into a receiving turret 41B through a receiving beam tube 49. A cylindrical lens 50 received the light and focuses it through a second prism 51 where it is turned through a further 90° toward a photo diode 52. A plate 53 with a 50 μm slit 53A limits the light reaching the photo diode. The prisms and lens are protected from the spray by waterproof shields 55 on the top of the turrets which can be removed to clean the prisms and lens. The prisms are seated on and sealed to their supports 56 to hold them in place and prevent liquid from getting into the electronics. The sensor unit 40 is self contained and a rechargeable battery pack 58 and an electronic controller 59 with a radio transmitter are housed in the base of the housing 60.

The sampling volume is set by the diameter of the beam tubes, the gap between the tubes and the width of the slit 53A. The depth of the sampling volume will be slightly less than the width of the slit as the beam is diverging, but this can be accommodated.

To ensure the droplet measurement is the same over the sampling area the light intensity should preferably be uniform. This can be achieved by ensuring the light source has a wide radiation angle (100° should be adequate) and the photo diode sensitivity is constant over a wide angle (100° should be adequate). It is also essential that any reflections from the beam tubes or elsewhere are eliminated by ensuring the relevant surfaces are non-reflective.

The arrangement of the second embodiment whilst robust and effective in the field still can encounter a number of errors in droplet diameter measurement. Firstly droplets that hit the edge of the beam tubes will be broken up and all or part of them will show as smaller droplets. Secondly, a droplet passing through the edge of the beam will show as a smaller droplet. And thirdly more than one droplet passing the slit at the same time will show as a single larger droplet, unless their shadows exactly overlap when one droplet will not be counted.

Figure 6:
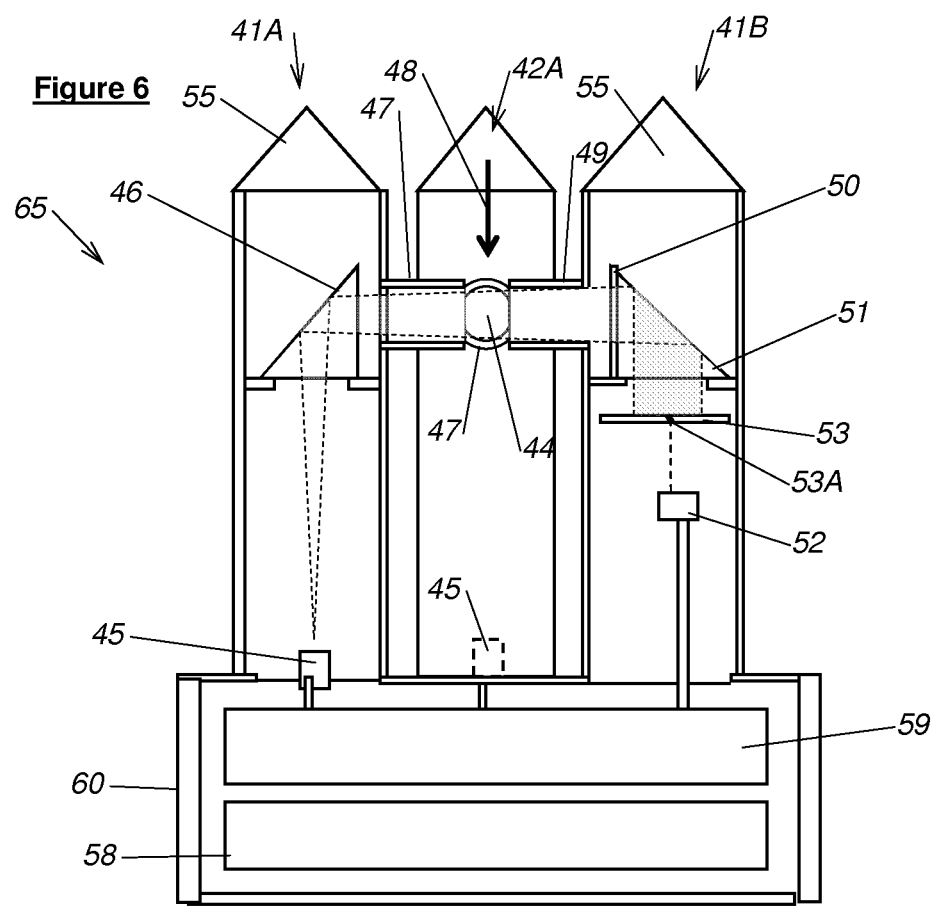
Figure 7:
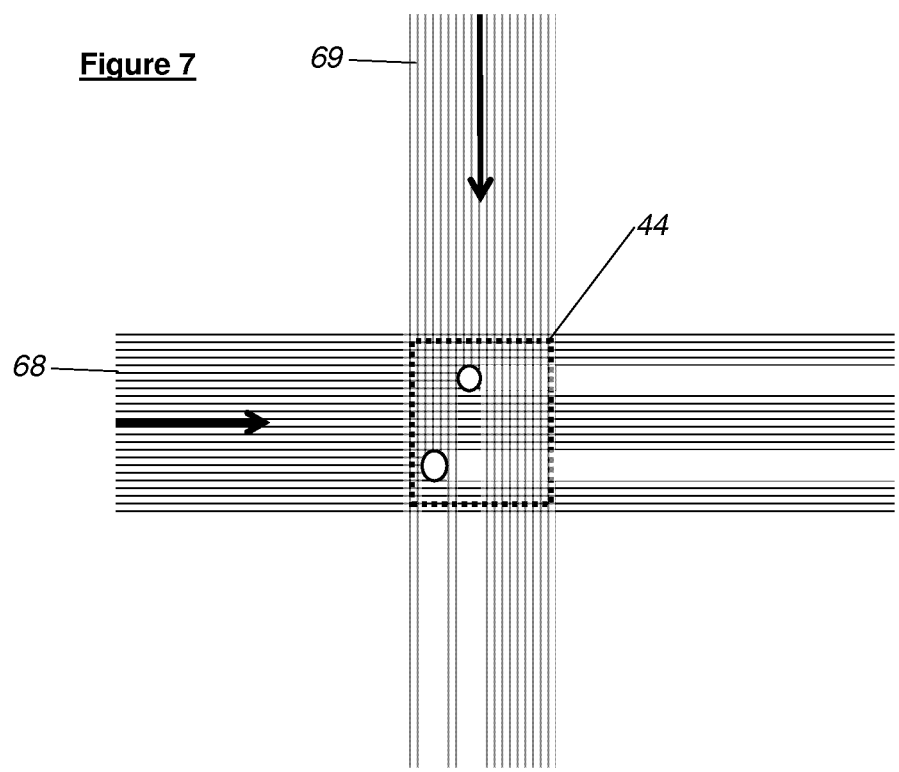
Figure 8:
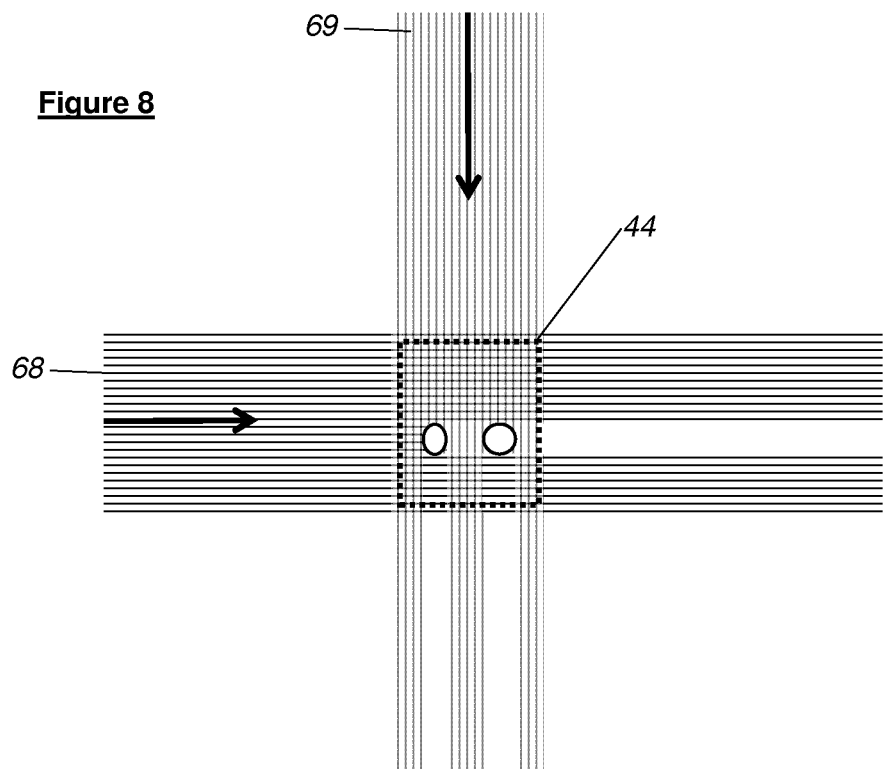

A significant improvement to address these issues is to have two light beams normal to each other to form the sampling area as schematically depicted in FIGS. 7 and 8. This is achieved in a third embodiment shown in FIGS. 5 and 6. This embodiment generally indicated 65 requires two light sources 45, two sets of prisms 46,51 and lenses 50, two slits 53A, two photo cells 52 and electronics 59 that can handle and compare both sets of beam data. The two sets of light sources, prisms etc. are equivalent to the second embodiment discussed above in the second embodiment and have been given like reference numerals. This improvement means the sampling area is now defined by the width of the light beams from each source where they cross so there is no physical edge to the sample area for droplets to hit and be broken up. The beam tubes will still limit the number of droplets each beam encounters as droplets far outside the sampling area may cause the count speed to be exceeded.

Figure 5:
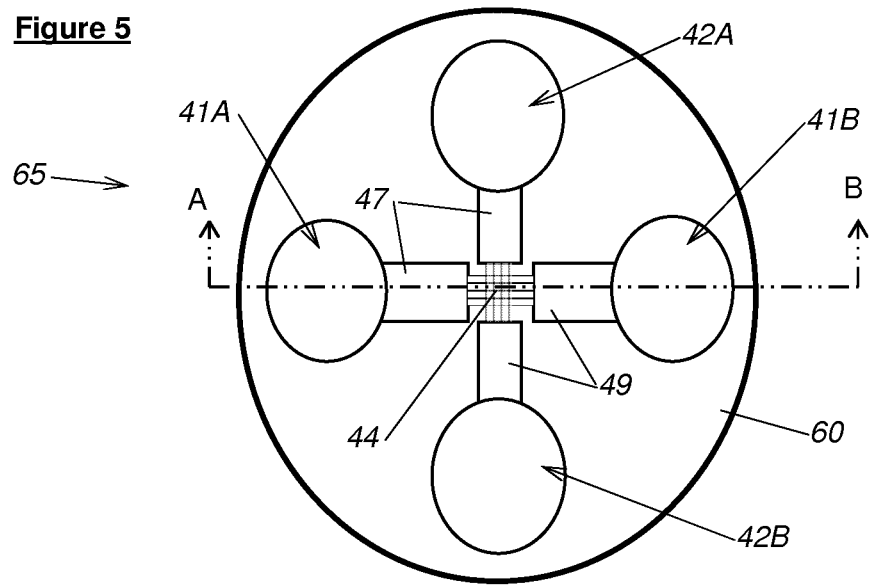

FIG. 5 shows a plan view looking down on the sensor unit and FIG. 6 shows the section on line AB. FIG. 5 shows two pairs of cooperating turrets 41A, 41B and 42A, 42B. Turret 41A transmits a first light beam 68 across the sampling area 44 that is received in turret 41B. Turret 42A transmits a second light beam 69 across the sampling area 44 at 90° to the first beam 68, the second beam being received in turret 42B. The components shown in FIG. 6 are essentially the same as those shown in FIG. 4 and like reference numerals are used. The perpendicular second beam 69 is generated, manipulated and detected in the same way using an equivalent set of components to that shown in FIG. 6.

A droplet in the sample area should show as the same size droplet in either beam, a droplet on the edge of the sample area will not show equally and can therefore be eliminated electronically. The sample area can be calculated knowing the droplet size so the ratio of droplet sizes can be corrected. The actual sampling area for each droplet size can be calculated. If the light beams for both channels are W wide then the actual sampling area for droplet size d would be (W−2d)(W−2d). If the beams are 7 mm wide then the sampling area for zero size droplets would be 49 mm². For 200 μm droplets it would be (7−0.4)(7−0.4)=43.6 mm². The number of 200 μm droplets would need to be corrected upwards by 49/43.6 i.e. about 12%. For droplets of 500 μm the correction would be 36%. If two droplets pass the slit at the same time and their shadows overlap (see FIG. 8) the total shadow they create will be different in each beam so they will be discounted. Droplets passing the slit at the same time but whose shadows do not overlap (see FIG. 7) will show the same in both channels and may be counted as a single larger droplet. Overall therefore the number of larger droplets counted will be slightly higher than the true number. From the size of the droplet and the time it takes to pass the slit the velocity of the droplet can be calculated. Two droplets passing the slit at the same time would have a calculated abnormal velocity and so could be eliminated electronically to mitigate this problem.

For convenience of use in an outdoor situation the device 65 will be self-powered, will measure droplet numbers and sizes, will digitise the data and will send this by radio to a hand held receiver and/or computer where the results can be analyzed and displayed in a variety of ways. The receiver may be in the form of a command unit and may be able to control several sensor units so results can be gathered from several areas at once.

Calibration of the device is important. The voltage signal from the photo diode can be calculated for each droplet size and the droplets of each size counted. From this the percentage volume for each droplet size can be calculated. The mean volume diameter and other details of the droplet spectrum can be derived from this information. The device can also be checked by passing virtual droplets of known sizes though the sampling area to give an independent calibration.

The invention claimed is:

1. A device to measure the characteristics of droplets within a stream of liquid droplets used in spraying comprising:
   a light source supplying light across the stream of droplets to be analysed;
   a detector to detect, from light passing straight across the stream of droplets, the change in the level of light caused by a droplet passing through the light produced by the light source, the droplet casting a shadow on the detector, thus generating a signal according to the change in light incident thereon; and
   a processor to analyse the characteristics of the droplets in the stream based on the signal produced by the detector;
   a panel disposed between the droplet stream and the detector and defining a horizontally disposed slit;
   a mask disposed between the droplet stream and the detector and defining a vertically disposed slit;
   wherein the light passes through the slit defined by the panel and through the slit defined by the mask, so that the change in level of light caused by the droplet shadow and detected by the detector is proportional to the diameter of the droplet.

2. A device as claimed in claim 1, wherein there is provided a sampling area through which droplets in the stream pass and through which light from the light source crosses the stream, and only droplets within the sampling area are measured as they pass therethrough.

3. A device as claimed in claim 2, wherein the sampling area has a volume of approximately 0.0025 cm³.

4. A device as claimed in claim 1, wherein the light source produces light in the infrared range.

5. A device as claimed in claim 1, wherein the light source is a point light source.

6. A device as claimed in claim 5, wherein the area of the point light source is 0.1 mm².

7. A device as claimed in claim 1, wherein the horizontally disposed slit is 50 μm wide.

8. A device as claimed in claim 1, wherein the device is encased in a housing.

9. A device as claimed in claim 1, further including a lens to focus the beam on to the light detector.

10. A device as claimed in claim 1, wherein the detector comprises a photo cell.

11. A device as claimed in claim 1, further comprising an amplifier to amplify the signal from the detector.

12. A device as claimed in claim 1, further comprising a current to voltage converter to convert electrical current produced by the detector into a voltage reading.

13. A device as claimed in claim 1, wherein the processor includes a counter to count the number of droplets.

14. A device as claimed in claim 1, wherein the processor further includes a comparator to separate droplets into different size ranges.

15. A device as claimed in claim 1, wherein an oscilloscope is provided to display the change in signal caused by a droplet and the processor is configured to measure the time to cross the horizontally disposed slit and to calculate the speed of the droplet.

16. A droplet measurement system comprising one or more device as claimed in claim 1 mounted on one or more sprayer and a remote command unit that receives data from the or each device and which is adapted to analyse and/or display this to an operator.

17. A droplet measurement system as claimed in claim 16, wherein the or each device includes a transceiver and is in wireless communication with the command unit.

\* \* \* \* \*